(12) United States Patent
Boege et al.

(10) Patent No.: US 8,831,715 B2
(45) Date of Patent: Sep. 9, 2014

(54) ECG HAND-HELD DEVICE

(75) Inventors: Henning Boege, Braunschweig (DE); Meinhard Schilling, Wolfenbuettel (DE); Martin Oehler, Braunschweig (DE)

(73) Assignee: Capical GmbH, Braunschweig (DE)

( * ) Notice: Subject to any disclaimer, the term of this patent is extended or adjusted under 35 U.S.C. 154(b) by 0 days.

(21) Appl. No.: 13/814,628

(22) PCT Filed: Aug. 10, 2011

(86) PCT No.: PCT/EP2011/004000
§ 371 (c)(1),
(2), (4) Date: Mar. 20, 2013

(87) PCT Pub. No.: WO2012/019760
PCT Pub. Date: Feb. 16, 2010

(65) Prior Publication Data
US 2013/0211272 A1    Aug. 15, 2013

(30) Foreign Application Priority Data
Aug. 12, 2010 (DE) .......... 10 2010 034 192

(51) Int. Cl.
| | | |
|---|---|---|
| *A61B 5/04* | (2006.01) | |
| *A61B 5/0408* | (2006.01) | |
| *A61B 5/00* | (2006.01) | |
| *A61B 5/0404* | (2006.01) | |
| *A61B 5/044* | (2006.01) | |

(52) U.S. Cl.
CPC ......... *A61B 5/0404* (2013.01); *A61B 2652/046* (2013.01); *A61B 2562/0209* (2013.01); *A61B 5/04085* (2013.01); *A61B 5/0006* (2013.01); *A61B 5/044* (2013.01)
USPC ........................................................ 600/523

(58) Field of Classification Search
CPC ..... A61B 5/044; A61B 5/0432; A61B 5/0006
USPC .................................................. 600/426, 523
See application file for complete search history.

(56) References Cited

U.S. PATENT DOCUMENTS

| | | |
|---|---|---|
| 2004/0215094 A1 | 10/2004 | Baumer |
| 2005/0101876 A1 | 5/2005 | Pearlman |
| 2006/0041196 A1* | 2/2006 | Matthews et al. ............. 600/393 |

FOREIGN PATENT DOCUMENTS

| | | |
|---|---|---|
| EP | 1 985 232 | 10/2008 |
| GB | 2 070 438 | 9/1981 |
| WO | 2009/041127 | 4/2009 |
| WO | 2009/087350 | 7/2009 |

OTHER PUBLICATIONS

Martin Oehler et al.; Capacitive ECG system with direct access to standard leads and body surface potential mapping; Biomedizinische Technik/Biomedical Engineering, vol. 54, Issue 6, 2009, pp. 329-335.

* cited by examiner

*Primary Examiner* — George Manuel
(74) *Attorney, Agent, or Firm* — Whitham Curtis Christofferson & Cook, PC

(57) ABSTRACT

An ECG device designed as a portable handheld device, with a housing which has a grip area and/or grip elements, wherein the grip area and/or the grip elements are designed to allow the ECG device to be held by an operator, and the ECG device has a sensor area, which is arranged outside the grip area and the grip elements and in which a plurality of ECG sensors in the form of capacitive electrodes is provided. Here, the ECG sensors are at least partially embedded in a foam block secured on the housing, and the ECG sensors are held by the foam block and supported elastically therein.

25 Claims, 5 Drawing Sheets

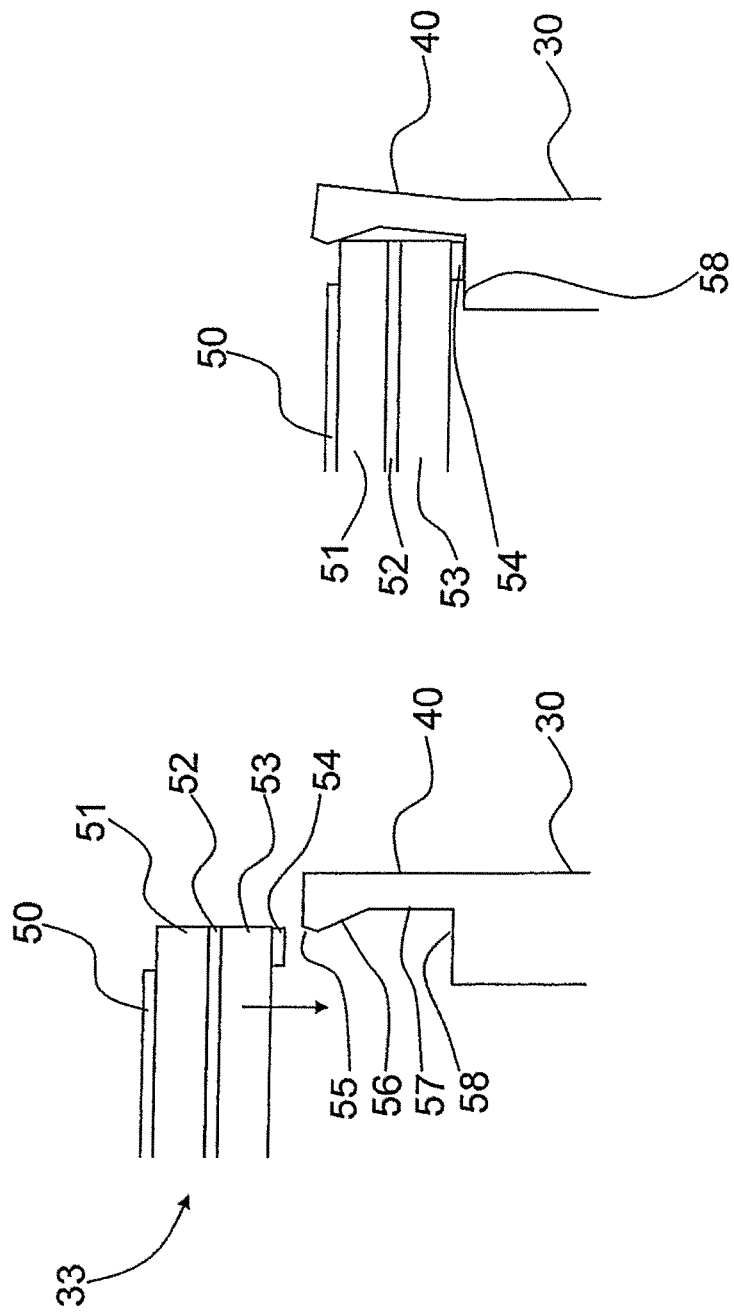

ECG HAND-HELD DEVICE

FIELD OF INVENTION

The invention relates to an ECG device designed as a portable handheld device.

BACKGROUND

The invention relates generally to the recording of electrocardiograms (ECG) using ECG sensors in the form of capacitive electrodes. Capacitive electrodes permit measurement of an electrocardiogram with the same results as with conventionally used galvanic electrodes. The advantage of capacitive electrodes is that no direct contact with the skin is necessary, and therefore measurements can even be carried out through clothing.

A capacitive ECG system for measuring standard leads and for body surface potential maps is already known from the publication by Martin Oehler, Meinhard Schilling and Hans Dieter Esperer, Biomed Tech 2009; 54:329-335.

SUMMARY

The object of the present invention is to improve the ECG device described in the aforementioned publication so that it is practical for everyday medical use.

This object is achieved by the invention set forth in Claim 1. Advantageous developments of the invention are set forth in the dependent claims.

The invention relates generally to an ECG device designed as a portable handheld device. Such a handheld device has the advantage that it is easy to handle and can be used everywhere, and in particular can also be transported to accident sites. Such a handheld device also has the advantage that, with a suitably compact design, it can be carried around permanently by physicians or in ambulances and emergency medical vehicles.

According to the invention, a portable handheld device of this kind is developed in the sense that the ECG sensors, which are provided in the form of capacitive electrodes, are at least partially embedded in a foam block secured on the housing. The ECG sensors are held by the foam block and supported elastically therein. It has been found that, by using a foam block of this kind, it is possible to solve a number of problems associated with a particularly practical design of an ECG device with capacitive electrodes. Thus, the foam first of all provides the desired mutual insulation of the electrodes. Moreover, the electrodes are already fixed and thus held in place by being embedded in the foam block, such that there is no need for further securing elements, which could impair the function and measuring accuracy of the capacitive electrodes. Moreover, the foam block is a simple and elegant way of providing elastic support of the ECG sensors, making them highly conformable to the shape of the human chest.

By contrast, the ECG device known from the aforementioned publication had capacitive electrodes mounted individually in a housing via helical springs, which arrangement proved unfavorable in practice, since the conformability of the electrode array to the human chest was inadequate, and since the spring mechanism also often caused jamming between the electrodes and the surrounding housing part.

All of these problems can now be solved in an inexpensive and elegant way by the invention according to Claim 1.

The foam block can be arranged in a recess of the housing, e.g. in a housing cutout. According to an advantageous development of the invention, the foam block is secured on a housing surface of the ECG device. This permits simple securing of the foam block on the housing, without large cutouts in the housing. Only a small opening is needed in the housing for the passage of the connection cable for the ECG sensors.

According to an advantageous development of the invention, the ECG sensors are arranged on the side of the foam block directed away from the housing. This has the advantage of minimizing the distance between the sensors and the human chest area that is to be recorded, and this leads to improved signal detection.

The ECG sensors can be embedded completely in the foam block, or only partially so, i.e. protruding slightly from the foam block. If the ECG sensors are embedded completely in the foam block, the ECG sensors can also be covered by a layer of foam.

According to an advantageous development of the invention, the ECG sensors are not covered by the material of the foam block, i.e. they are so to speak visible from the outside in a plan view of the foam block. This has the advantage of maximizing the detection sensitivity of the ECG sensors.

According to an advantageous development of the invention, the ECG sensors, on the side of the foam block directed away from the housing, are arranged at approximately the same distance to the surface of the foam block directed away from the housing. In this way, it is possible to ensure uniform signal detection across the plurality of the ECG sensors.

The surface of the foam block directed away from the housing can be flat, for example.

According to an advantageous development of the invention, the foam block, on its side directed away from the housing, has a convex shape. The convex shape of the foam block on its side directed away from the housing can be produced, for example, by a suitably convex shaping of the securing surface on the housing of the ECG device that serves for the attachment of the foam block. It is equally possible for the foam block itself to be correspondingly convexly shaped.

According to another advantageous development of the invention, the ECG sensors are arranged along a convexly shaped surface, in particular along the same convex shape of the foam block on its side directed away from the housing.

The convex shape advantageously permits improved conformability of the sensor area of the ECG device to differently shaped chest areas in humans. In particular, this permits conformability to concave chest shapes and, with a suitably soft configuration of the foam, also to convex chest shapes.

According to an advantageous development of the invention, a protective sleeve which is impermeable to liquid, washable and can be disinfected by wiping is stretched over the foam block and the ECG sensors arranged in the latter. This has the advantage that the ECG sensors and the foam are protected from liquids which, for example, are used for cleaning and disinfecting. Moreover, the protective sleeve permits easy cleaning and disinfecting of the ECG device. Advantageously, the protective sleeve can be disinfected by wiping, i.e. it can be disinfected in accordance with the medical requirements simply by wiping it with a disinfectant.

The protective sleeve can be made of a textile material, e.g. a woven or a nonwoven, or of leather, or of a pore-free, closed synthetic material. Suitable materials for the protective sleeve are, for example, Latex, microfibers or Goretex.

According to an advantageous development of the invention, the protective sleeve is made of a non-statically chargeable synthetic material. This has the advantage of reliably avoiding undesired effects on the signals of the ECG sensors as a consequence of static charges. The protective sleeve can be made of a polyurethane film, for example. It has been found that plaster material, which is also used for wound plaster, is well suited for this purpose.

The invention therefore also relates to the use of a polyurethane film as a protective sleeve for protecting the foam block of an ECG device.

According to an advantageous development of the invention, the protective sleeve can be secured on the housing of the ECG device by means of releasable adhesive and/or Velcro tape. For this purpose, the protective sleeve and/or the housing can have corresponding adhesive points or adhesive strips.

According to an advantageous development of the invention, the protective sleeve is designed as a disposable article that can be used just once. This has the advantage that rapid change of protective sleeve is possible and no cleaning is necessary.

In principle, any desired flexible foam can be used for the foam block, e.g. PE foam. It is possible to use soft foam materials and also harder foam materials. With harder foam materials, the required elasticity and flexibility, which is needed for a necessary adaptation of the ECG sensor area to different human chest shapes, can be obtained, for example, by making cuts or slits in the foam material.

According to an advantageous development of the invention, the foam block has a compressive strength in the range from 2 to 30 RG. In this way, the foam block is soft enough for flexible adaptation to different human chest shapes, and yet the foam block is stable enough to safely hold and support the ECG sensors.

According to an advantageous development of the invention, the foam block has an overall density in the range from 25 to 45 kg/m$^3$. This permits the use of sufficiently stable yet flexible foam materials.

According to an advantageous development of the invention, the foam block is made completely or partially of viscoelastic foam. Latex can be used, for example, as viscoelastic material. The use of viscoelastic foam has the advantage that the foam block can conform well to the shape of a patient's body and, because of the special properties of the viscoelastic foam and on account of the body heat, it maintains the adopted shape for quite a long time and thus conforms adaptively to the shape of the body. This has the advantage that the ECG device is easier to handle and, after suitable shaping of the viscoelastic foam, can be held on the patient with less force being applied. In addition, viscoelastic foam is easy to work, in particular at low temperatures.

The ECG device can already be equipped with input means and display means, e.g. to input necessary settings and to display the ECG signals. However, it has been found that this can make the ECG device quite heavy and unwieldy, and therefore, for use as a portable handheld device, it is advantageous to design the ECG device simply as an ECG signal detector without its own display unit for showing the recorded ECG signals. In this case, the ECG device can be operated wirelessly and has an integrated power supply. This permits the greatest possible flexibility of use and handling of the ECG device in practical medical application.

According to an advantageous development of the invention, the ECG device has a wireless data interface via which the recorded ECG data can be transferred to a separate evaluation computer or a separate display unit. For example, the ECG device can be equipped with a memory that permits storage of the recorded ECG signals for an entire ECG recording. Subsequent to the recording, the stored ECG data are then transferred to an evaluation computer or to a separate display unit, e.g. via the wireless data interface or a cable. In this case, an evaluation of the recorded ECG signals can be performed at a later stage on the evaluation computer or on the separate display unit. According to an advantageous development of the invention, the ECG device is set up for wireless data transfer of the recorded ECG data via the wireless data interface during the ECG recording. This allows the recorded ECG data to be displayed on a separate evaluation computer or separate display unit contemporaneously with the recording, i.e. in real time.

According to an advantageous development of the invention, the housing, on the side directed away from the ECG sensors, has at least one control element and/or a signal indicator element, which is not configured for the ECG signal display. The signal indicator element can, among other things, inform the operator as to whether the ECG device is correctly set up for an ECG recording on a human chest. The signal indicator element can be designed, for example, in the form of a light-emitting diode or several light-emitting diodes, e.g. light-emitting diodes in different colors, via which an operator is informed, for example on the basis of a red/green difference, as to whether the ECG device is correctly set up for an ECG recording on a human chest. The signal indicator element can also be an alphanumeric LCD display. The control element can be a switch or a button, for example, via which certain settings can be adjusted, such as sensitivity or mode of presentation.

According to an advantageous development of the invention, one, some or all of the ECG sensors has/have a cylindrical cup-shaped metal part with a substantially closed bottom and, directed away from the bottom, an end area designed like a crown with snap-fit fastening elements. Moreover, a sensor plate which has at least three mutually insulated conductor track levels is provided and can be inserted or snapped into the cup-shaped metal part.

Moreover, the invention also relates to an ECG sensor in the form of a capacitive electrode with the above-described advantageous structure.

Such a structure of an ECG sensor has the advantage that the sensor can be manufactured in a simple and efficient way and is in particular suitable for inexpensive mass production.

According to an advantageous development of the invention, the sensor plate, on its side directed toward the inside of the cup, i.e. toward the inside of the cup-shaped metal part, has a ring-shaped conductor track via which an electrical contact between the sensor plate and the cup-shaped metal part is produced after the sensor plate has been snapped into the cup-shaped metal part. The cup-shaped metal part serves here as a screen against external interference signals.

This has the advantage that the electrical contact, required for the screening, between the sensor plate and the cup-shaped metal part can also be produced easily and quickly, namely by simply snapping the sensor plate into the cup-shaped metal part. In this way, mass production of the ECG sensor can be further optimized.

According to an advantageous development of the invention, the ECG device has at least one electrical connecting element for the connection of at least one external ECG sensor. The electrical connecting element can be designed, for example, as a socket for receiving an electric plug. This has the advantage that the ECG device can be expanded, in terms of its function, by external ECG sensors. The external ECG sensor can, for example, be designed as a capacitive electrode or as a conventional galvanic electrode.

According to an advantageous development of the invention, the ECG device has at least one electrical connecting element for the connection of an external clamp electrode. By means of the clamp electrode, it is possible, for example, to establish a potential equalization between a patient, on whom an ECG is to be recorded, and the ECG device.

According to an advantageous development of the invention, the clamp electrode has both a potential equalization contact and also an external ECG sensor. The external ECG sensor and the potential equalization electrode can be connected to the ECG device via a common multi-wire connection cable. This permits an expansion of the function of the ECG device via an external ECG sensor and the potential equalization electrode, without a large number of connection cables having to be connected. In this way, it is possible to avoid cables becoming entangled.

The invention also covers an external clamp electrode which has both a potential equalization electrode and also an external ECG sensor. The external ECG sensor is advantageously likewise designed as a capacitive electrode.

According to an advantageous development of the invention, at least one external ECG sensor is connected permanently to the ECG device via a cable. The housing of the ECG device contains a roll-up mechanism for the cable. This permits simple and rapid stowage of the cable, if appropriate together with the external ECG sensor, in the housing of the ECG device. In this way, the ECG device, when not in use, is maneuverable and easy to transport. A further advantage is that the external ECG sensor and the connection cable are always carried around with the device and cannot get forgotten.

According to an advantageous development of the invention, at least one satellite electrode arrangement can be connected to the ECG device and has a plurality of ECG sensors in the form of capacitive electrodes. It is possible, for example, to use the capacitive electrodes according to the embodiments explained above. For this purpose, the ECG device has a connection that is configured for contacting the plurality of ECG sensors of the satellite electrode arrangement. The satellite electrode arrangement has the advantage of creating a kind of external sensor pathway which provides additional possibilities of ECG signal detection, in particular with additional flexibility in the handling and arrangement of the satellite electrode arrangement. The satellite electrode arrangement can be designed similarly to the ECG sensors arranged in the sensor area of the ECG device, e.g. on a housing of a satellite electrode arrangement, embedded in a foam block secured on the latter. Advantageously, the structure of the satellite electrode arrangement is slightly smaller than the ECG device.

The invention is explained in more detail below on the basis of illustrative embodiments and with reference to drawings, in which:

DESCRIPTION OF THE DRAWINGS

FIGS. 4-6 show details of the structure of the ECG sensor.

DETAILED DESCRIPTION

In the figures, the same reference signs are used for elements corresponding to one another.

Figure 1:
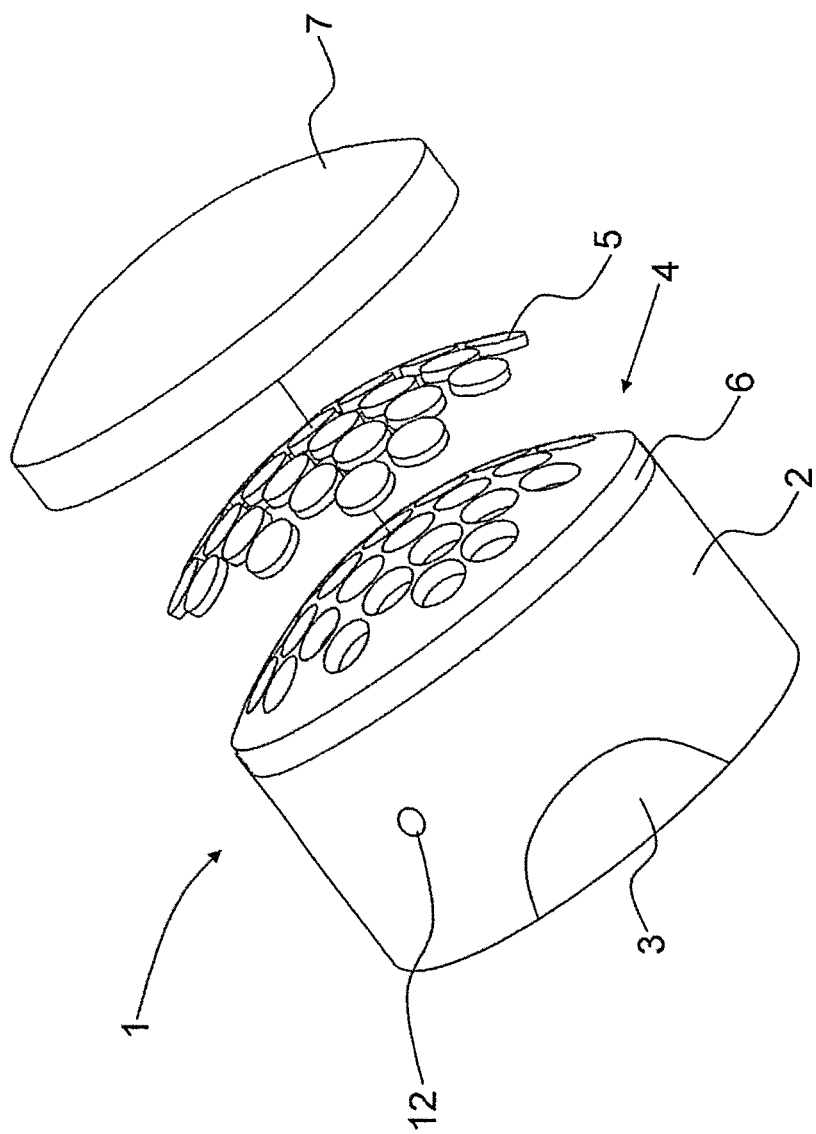
FIG. 1 shows an exploded view of an ECG device.

FIG. 1 shows a perspective view of an ECG device 1 designed as a portable handheld device. The ECG device 1 has a housing 2 with a grip area 3. A sensor area 4 is provided on a side of the housing outside the grip area 3. A foam block 6 is arranged in the sensor area 4. The foam block 6 is secured on the housing 2, on a surface of said housing 2 directed away from the grip area. A plurality of ECG sensors 5 is embedded in the foam block 6, e.g. in the manner of a matrix. As can be seen, the foam block 6 bulges away from the housing 2, i.e. has a convex shape. A protective sleeve 7 is stretched over the foam block 6 and over the electrodes 5 embedded in the latter.

The housing 2 already accommodates all the components needed to record ECG signals via the ECG sensors 5, e.g. evaluation electronics, an interface for data transfer, in particular a wireless interface, and a power supply. A side wall of the housing 2 is also provided with an electrical connecting element 12, e.g. a connecting socket, via which the external components, e.g. an external ECG sensor, can be connected to the ECG device 1.

Figure 2:
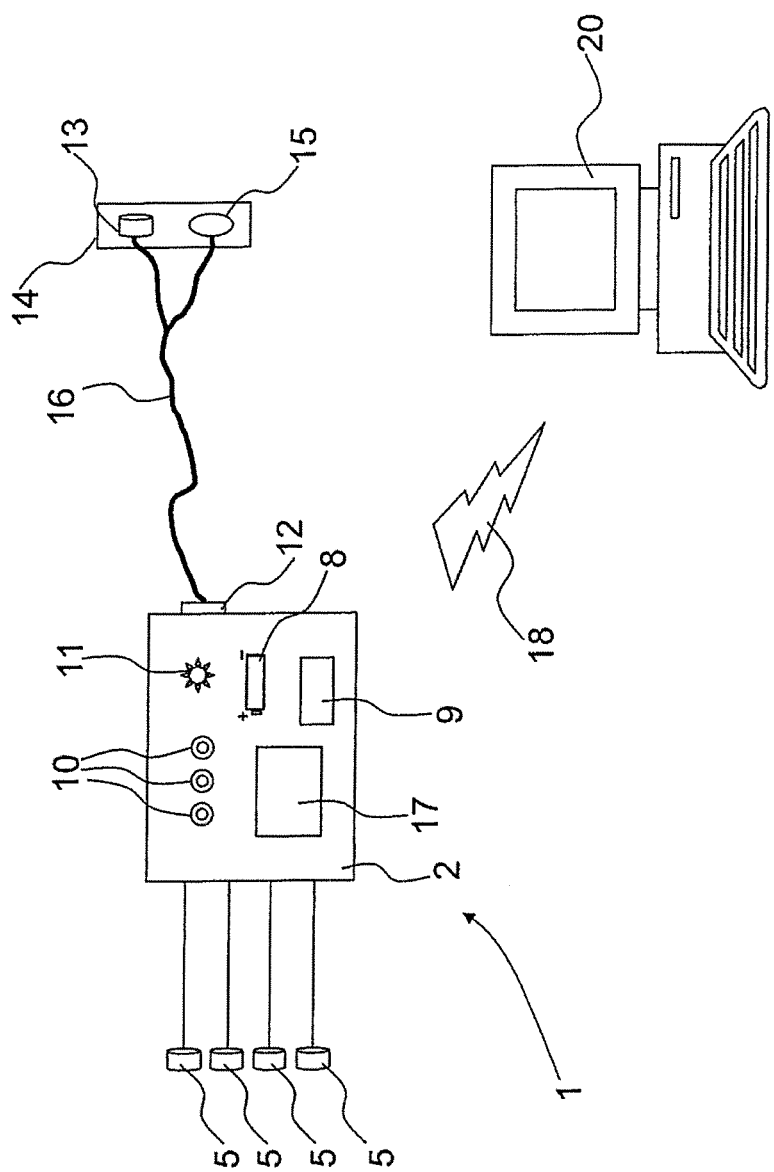
FIG. 2 shows a schematic view of another embodiment of the ECG device and an evaluation computer.

FIG. 2 shows another embodiment of the ECG device 1 in a schematic view in the manner of a block diagram. The ECG device 1 according to FIG. 2 furthermore has the same structure as the ECG device 1 according to FIG. 1. In FIG. 2, the ECG sensors 5 are depicted schematically and merely by way of example on the basis of four sensors.

The ECG device 1 according to FIG. 2 has an integrated power supply 8, e.g. an accumulator. The accumulator can be charged via a charging connection arranged on the housing 2. Alternatively, it is possible to charge the accumulator 8 instead via a separate charging connection by inductive coupling of electrical energy into the housing 2. In this case, an induction receiver coil is provided in the housing 2.

An evaluation circuit 17 and a wireless interface module 9 are also provided in the housing 2. The evaluation circuit 17 evaluates the signals of the ECG sensors 5 and transfers the evaluated information via the wireless interface module 9 to an evaluation computer 20 over a wireless data transfer path 18. The wireless interface module 9, which can be designed as a Bluetooth module for example, permits bidirectional transfer of data between the ECG device 1 and the external evaluation computer 20. Thus, for example, recorded ECG signals can be transferred from the ECG device 1 to the external evaluation computer 20, and, for example, measurement settings can be transferred from the external evaluation computer 20 to the ECG device 1. The received ECG data can then be displayed graphically on the evaluation computer 20 by means of suitable software.

The ECG device 1 also has an indicator element 11, arranged on the rear face of the housing for example, and three control elements 10, for example in the form of buttons. Certain settings can be made on the ECG device 1 via the buttons 10. Certain operating states of the ECG device can be shown by the indicator element 11, e.g. readiness for operation, insufficiently charged accumulator 8, or the correct orientation of the electrodes 5 on a patient.

The ECG device 1 can also have a larger graphics display, which is arranged on the rear face, for example, and on which the recorded ECG signals can be shown directly. The display can advantageously be part of a tablet PC which is arranged on the rear face of the ECG device 1 and which, in addition to displaying the ECG signals, also permits extended possibilities as regards setting the ECG device.

The ECG device 1 according to FIG. 2 also has the electrical connecting element 12. FIG. 2 shows how an external clamp electrode 14 is connected to the connecting element 12 via a multicore electric line 16. The clamp electrode 14 has an external ECG sensor 13, which can be configured similarly to the ECG sensors 5, and also a potential equalization electrode 15.

The satellite electrode arrangement described at the outset can be connected to the ECG device 1 via an electric line in a manner similar to the above-described clamp electrode 14.

For this purpose, the electrical connecting element 12 additionally has electrical contacts for contacting the plurality of ECG sensors of the satellite electrode arrangement.

Figure 3:
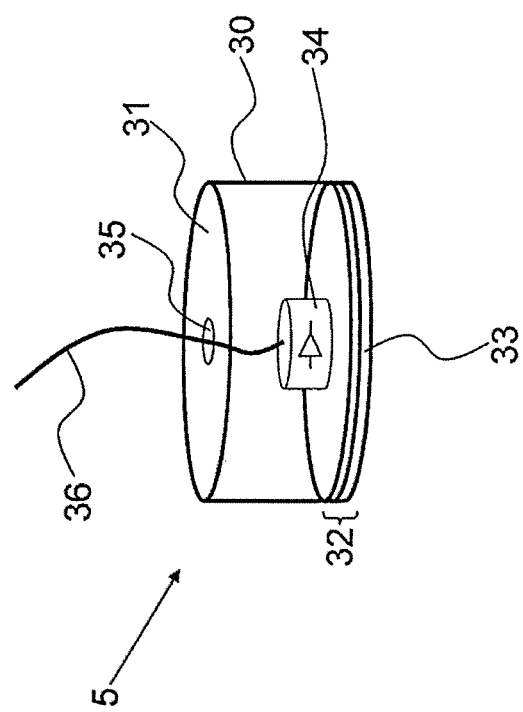
FIG. 3 shows an ECG sensor.

FIG. 3 shows the structure of an ECG sensor 5 in the form of a capacitive electrode with further details. The ECG sensor 5 is composed of a cup-shaped metal part 30 and a sensor plate 33. Here, the sensor plate 33 is inserted into the cup-shaped metal part 30 by being secured with a snap fit in an end area 32 of the cup-shaped metal part 30. On its side arranged inside the cup-shaped metal part 30, the sensor plate 33 has a signal processing circuit 34 which contains, for example, an impedance converter, an amplifier and a filter circuit. The signal processing circuit 34 is connected to the evaluation circuit 17 in the housing 2 via a connection cable 36, which is routed through an opening 35 arranged in a bottom 31 of the cup-shaped metal part 30.

Figure 4:
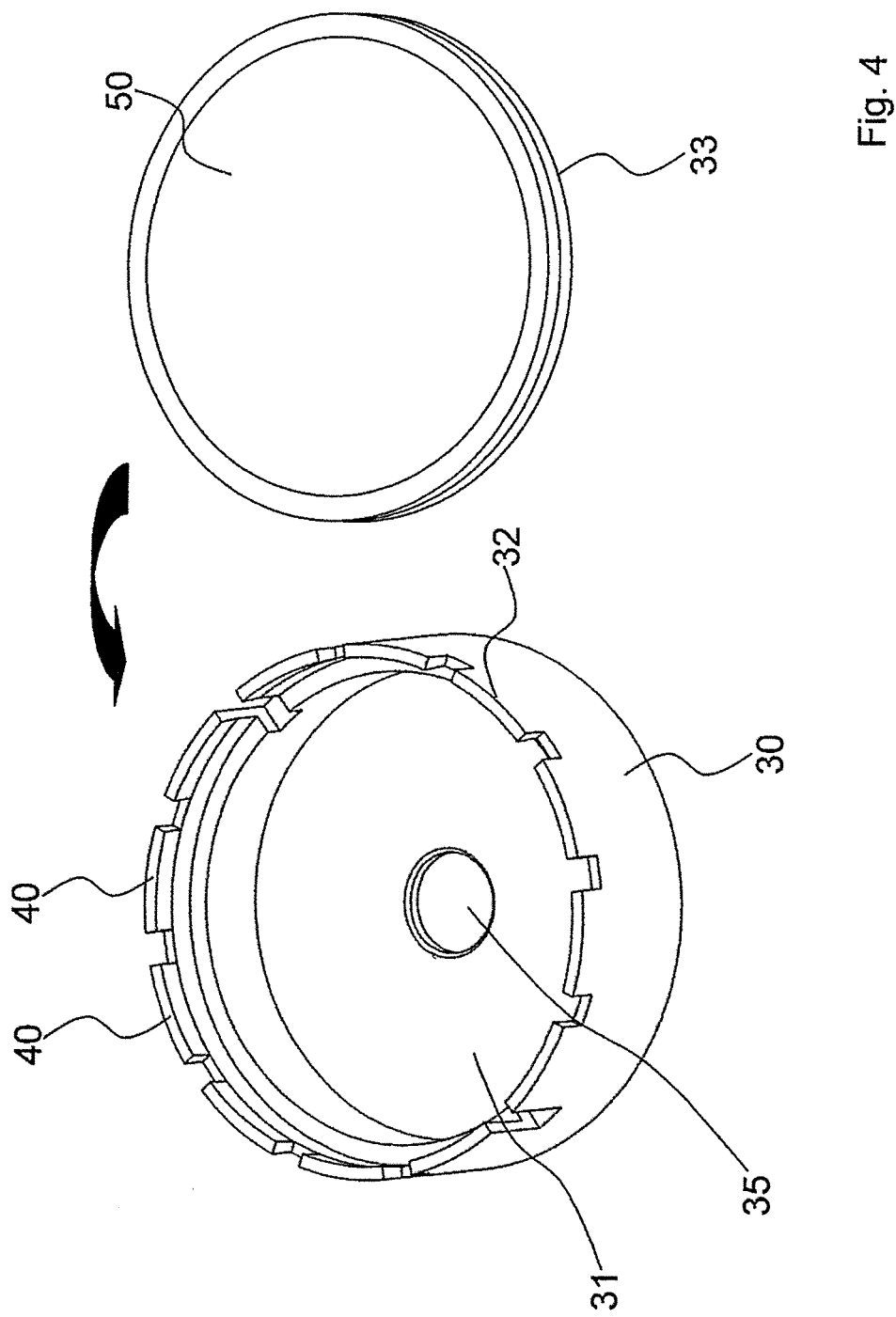

FIG. 4 shows the cup-shaped metal part 30 of the ECG sensor 5, and also the sensor plate 33 before its insertion into the cup-shaped metal part 30. As can be seen, the cup-shaped metal part 30 is designed with a substantially closed bottom 31, in which the through-opening 35 is provided for passage of the cable 36. In an end area 32, the cup-shaped metal part 30 has snap-fit fastening elements 40, which are arranged circumferentially like a crown in the end area 32. The sensor plate 33 has an electrode layer 50 which faces outward, i.e. not toward the inside of the cup-shaped metal part 30, and which, for example, can be provided with an insulation. The electrode layer 50 serves here as the sensor surface of the capacitive ECG sensor. The cup-shaped metal part 30 serves as a screening housing against external interference fields.

FIGS. 5 and 6 show in more detail both the snap-fit mechanism and also the exact structure of the sensor plate 33. In FIGS. 5 and 6, the sensor plate 33 and the side wall of the cup-shaped metal part 30 are shown in sectional views.

As can be seen in FIG. 5, the sensor plate 33 has an at least five-layer structure. Starting from the top face of the sensor plate 33, facing outward after placement in the cup-shaped metal part 30, the sensor plate 33 has the electrode layer 50, below this a first insulating layer 51, below the latter an electrically conductive screening layer 52, below the latter a second insulating layer 53, and below the latter, finally, an electrically conductive contacting layer 54. The sensor plate 33 can, for example, be produced particularly inexpensively as a circuit board formed with three conductor track levels. In this case, the layers 50, 52, 53 are formed as conductor track levels of the circuit board, the insulating layers 51, 53 as levels made from the circuit board material, e.g. of glass-fiber-reinforced epoxy.

The signal processing circuit 34, which is not shown in FIGS. 5 and 6, can be formed directly on the underside of the second insulating layer 53 with further conductor tracks and corresponding electronic components arranged thereon.

The electrode layer 50 is connected to the signal processing circuit 34 by means of plated-through holes. The screening layer 52 is similarly connected to the contacting layer 54 by plated-through holes. The contacting layer 54 is advantageously formed as a ring-shaped conductor track which surrounds the elements of the signal processing circuit 34 that lie in between.

FIG. 5 also shows the basic configuration of the snap-fit elements 40. Starting from the open face of the cup-shaped metal part 30 into which the sensor plate 33 is inserted, the snap-fit element 40 first has a short beveled area 55, the bevel pointing to the inside of the cup. This area is followed by a second beveled area 56, which has a bevel pointing in the opposite direction and which, in the direction of insertion of the sensor plate 33, is slightly longer than the first beveled area 55. There then follows a spring area 57, in which the wall thickness of the snap-fit element is approximately constant. However, this is not essential. The important thing is that the wall thickness in the spring area 57 is sufficiently small to ensure a sufficient spring action for the snap-in effect of the sensor plate 33. The spring area 57 is followed by an approximately horizontal abutment face 58.

FIG. 6 shows the cup-shaped metal part 30 with the sensor plate 33 inserted. As can be seen, the snap-fit fastening element 40 is bent slightly outward by the snap-fit action and is thus under the effect of a pretensioning by which the sensor plate 33 is held in the cup-shaped metal part 30. Here, the sensor plate 33 bears on the abutment face 58, which provides a defined abutment for the sensor plate 33. As a result of the way in which the contacting layer 54 is arranged, this contacting layer 54 at the same time produces an electrical contact between the screening layer 52 and the cup-shaped metal part 30 via the abutment face 58. In this way, the screening layer 52 is electrically connected to the cup-shaped metal part 30. In this way, a Faraday cage is in practice formed around the signal processing circuit 34.

The invention claimed is:

1. An ECG device comprising:
a housing which has a grip area and/or grip elements, the grip area and/or the grip elements are designed to allow the ECG device to be held by an operator;
a sensor area, which is arranged outside the grip area and the grip elements and in which a first plurality of ECG sensors in the form of capacitive electrodes is provided; and,
a foam block secured on the housing in the sensor area,
wherein the first plurality of ECG sensors are secured on or in the foam block and are supported elastically by means of the foam block,
whereby the ECG device is designed as a portable hand-held device.

2. The ECG device according to claim 1, wherein the foam block is secured on a housing surface of the ECG device.

3. The ECG device according to claim 1, wherein the first plurality of ECG sensors are arranged on a side of the foam block directed away from the housing.

4. The ECG device according to claim 3, wherein the first plurality of ECG sensors, on the side of the foam block directed away from the housing, are not covered by the foam block.

5. The ECG device according to claim 1, wherein a side of the foam block directed away from the housing has a convex shape.

6. The ECG device according claim 1, further comprising:
a protective sleeve, which is impermeable to liquid, washable and can be disinfected by wiping, is stretched over the foam block,
wherein the first plurality of ECG sensors are arranged in the foam block.

7. The ECG device according to claim 6, wherein the protective sleeve is secured on the housing by means of releasable adhesive and/or Velcro tape.

8. The ECG device according to claim 1, further comprising:
a protective sleeve, which is made of a non-statically chargeable synthetic material, is stretched over the foam block,
wherein the first plurality of ECG sensors are arranged in the foam block.

9. The ECG device according to claim 8, wherein the protective sleeve is made of a polyurethane film.

10. The ECG device according to claim 1, wherein the foam block has a compressive strength in the range from 1.5 to 5 kPa.

11. The ECG device according to claim 1, wherein the foam block has an overall density in the range from 10 to 45 kg/m$^3$.

12. The ECG device according to claim 1, wherein the foam block is made completely or partially of viscoelastic foam.

13. The ECG device according to claim 12, wherein the foam block has a layer of viscoelastic foam on a side of the foam block directed away from the housing.

14. The ECG device according to claim 1 further comprising:
a wireless data interface via which the recorded ECG data is transferred to a separate evaluation computer or a separate display unit.

15. The ECG device according to claim 14, wherein the ECG device is designed as a simple ECG signal detector which does not have its own display unit for showing the recorded ECG signals, which is operated wirelessly, and has an integrated power supply.

16. The ECG device according to claim 1, wherein the housing, on a side of the housing directed away from the sensor area, has at least one control element and/or a signal indicator element, which is not configured for a ECG signal display.

17. The ECG device according to claim 1, wherein at least one of the first plurality of ECG sensors has a cylindrical cup-shaped metal part with a bottom, an end area (32) designed like a crown with snap-fit fastening elements, wherein the end area is directed away from the bottom, and a sensor plate which has at least three conductor track levels, separated from one another by insulation layers, wherein the sensor plate can be inserted or snapped into the cylindrical cup-shaped metal part.

18. The ECG device according to claim 17, wherein the sensor plate, on a side of the sensor plate directed toward the inside of the cylindrical cup-shaped metal part, has a ring-shaped conductor track via which an electrical contact between the sensor plate and the cylindrical cup-shaped metal part is established after the sensor plate has been snapped into the cylindrical cup-shaped metal part.

19. The ECG device according to claim 1 further comprising:
at least one electrical connecting element for the connection of at least one external ECG sensor.

20. The ECG device according to claim 1 further comprising:
at least one electrical connecting element for the connection of at least one potential equalization electrode.

21. The ECG device according to claim 20, wherein the at least one potential equalization electrode and an external ECG sensor is connected in the form of a clamp electrode, and wherein the external ECG sensor and the potential equalization electrode is connected to the ECG device via a common multi-wire connection cable.

22. The ECG device according to claim 1 further comprising:
at least one external ECG sensor is connected permanently to the ECG device via a cable,
wherein the housing of the ECG device contains a roll-up mechanism for the cable.

23. The ECG device according to claim 1, further comprising:
at least one satellite electrode arrangement which is connected to the ECG device, and the at least one satellite electrode arrangement has a second plurality of ECG sensors in the form of capacitive electrodes.

24. The ECG device according to claim 1 further comprising:
a polyurethane film used as a protective sleeve for protecting the foam block.

25. The ECG device according to claim 1, wherein the distance between neighboring ECG sensors in the sensor area is less than the average width of an ECG sensor.

* * * * *